United States Patent [19]

Wheaton et al.

[11] 4,224,223

[45] Sep. 23, 1980

[54] PREPARATION OF ALKYLENE CARBONATES FROM OLEFINS

[75] Inventors: Gregory A. Wheaton, Swedesboro; Jar-lin Kao; Ming N. Sheng, both of Cherry Hill, all of N.J.

[73] Assignee: Atlantic Richfield Company, Los Angeles, Calif.

[21] Appl. No.: 68,997

[22] Filed: Aug. 23, 1979

[51] Int. Cl.$^2$ .................. C07D 317/36; C07D 317/38
[52] U.S. Cl. ................................................. 260/340.2
[58] Field of Search ....................................... 260/340.2

[56] References Cited

U.S. PATENT DOCUMENTS

| | | | |
|---|---|---|---|
| 3,025,305 | 3/1962 | Verdol | 260/340.2 |
| 3,923,842 | 12/1975 | Wu | 260/340.2 |
| 4,009,183 | 2/1977 | Fumagalli et al. | 260/340.2 |

Primary Examiner—Norma S. Milestone
Attorney, Agent, or Firm—Delbert E. McCaslin

[57] ABSTRACT

A process for the preparation of a cyclic alkylene carbonate ester which comprises reacting in a liquid phase a cyclic or linear olefin having from 2 to 15 carbon atoms with carbon dioxide at a temperature of from 50 to 160° C., at a total pressure of from 200 to about 2,000 psig and a pH value of between about 4 and 8, in the presence of oxygen or an oxygen-containing gas and a catalytic amount of a mixture of (a) iodine or an iodide of a metal selected from Groups IA, IB, IIA, IIB, VB, VIIB and VIII of the Periodic Table of Elements and (b) a catalytic iron compound, copper compound of mixture thereof deposited on an inert supporting material, and recovering resulting cyclic alkylene carbonate ester.

7 Claims, No Drawings

PREPARATION OF ALKYLENE CARBONATES FROM OLEFINS

BACKGROUND OF THE INVENTION

The cyclic carbonate esters of vicinal diols are well known in the art and may be prepared by reacting the corresponding chlorohydrins with either sodium bicarbonate under carbon dioxide pressure or with an alkali metal carbonate. Such esters can also be produced by the reaction between vicinal chlorohydrins and diethylamine under carbon dioxide pressure. All of these processes require the use of a stoichiometric amount of base.

Another route for the preparation of cyclic alkylene carbonate esters involves the reaction between an alkylene epoxide and carbon dioxide at high pressure in liquid phase in the presence of a catalyst. Typical catalysts include quaternary ammonium halides, quaternary ammonium hydroxides, sodium bicarbonate, ion exchange resins, bis-(aminoethoxy)tin compounds and polyhalogenated 5- or 6-membered ring hydrocarbons. Such processes as these require the use of expensive alkylene epoxide as the starting material for the cyclic carbonate ester production.

Two routes for production of cyclic carbonate esters directly from olefins have appeared in the literature. According to U.S. Pat. No. 3,025,305, an olefin, carbon dioxide and oxygen are reacted in the liquid phase in the presence of a dual catalyst system. One component of the catalyst is a salt or other compound of a heavy metal and the second catalyst component is a quaternary ammonium hydroxide or halide. According to U.S. Pat. No. 4,009,183, cyclic carbonate esters are produced by the reaction between an olefin, carbon dioxide and oxygen in the presence of iodine or a metal iodide and an oxygen carrier such as activated manganese dioxide or sodium nitrite. In each of these routes the rate of carbonate ester formation is slow. In the second route, a second step is required in order to regenerate the oxygen carrier which is used in stoichiometric excess.

SUMMARY OF THE INVENTION

The present invention relates to the preparation of cyclic alkylene carbonate esters and comprises reacting in a liquid phase a cyclic or linear olefin having from 2 to 15 carbon atoms with carbon dioxide at a temperature of from 50° to 160° C., at a total pressure of from 200 to about 2,000 psig and a pH value of between about 4 and 8, in the presence of oxygen or an oxygen-containing gas and a catalytic amount of a mixture of (a) iodine or an iodide of a metal selected from Groups IA, IB, IIA, IIB, VB, VIIB and VIII of the Periodic Table of Elements and (b) a catalytic iron compound, copper compound or mixture thereof deposited on an inert supporting material, and recovering resulting cyclic alkylene carbonate ester.

The process of the present invention produces the cyclic alkylene carbonate esters with high selectivity at high rates directly from the corresponding olefin in one step without the use of oxygen carriers which require regeneration in a separate stage or large amounts of basic metal carbonates. In addition, this process provides for much more efficient use of the catalytic iron compound, copper compound or mixture thereof.

DETAILED DESCRIPTION OF THE INVENTION

In accordance with the present invention, a cyclic or linear olefin having from 2 to 15 carbon atoms is reacted in an autoclave or any other pressure reactor with carbon dioxide and oxygen at elevated temperature and pressure in the presence of a catalyst comprising iodine or an iodide of a metal selected from Groups IA, IB, IIA, IIB, VB, VIIB and VIII of the Periodic Table of Elements and a catalytic iron compound, copper compound or a mixture thereof deposited on an inert supporting material. The order of addition of the reactants, catalysts, solvents, etc. is not critical.

Any cyclic or linear olefin having from 2 to 15 carbon atoms may be employed in the present process. Preferably, the olefin contains from 2 to about 6 carbon atoms and even more preferably, the olefin is an α-olefin, i.e. contains a terminal carbon-to-carbon double bond. Ethylene, propylene, butylenes, pentenes, hexenes and cyclohexene are examples of especially preferred olefins.

The metal iodides which may be employed in the catalytic system for this process are selected from groups IA, IB, IIA, IIB, VB, VIIB, and VIII of the Periodic Table of Elements. The metal iodides which may be employed include, for example, lithium iodide, potassium iodide, cuprous iodide, calcium iodide, magnesium iodide, zinc iodide, cadmium iodide, vanadium iodide, manganese iodide, iron iodide, cobalt iodide, and the like. The amount of metal iodide which may be employed in this invention is generally in the range of from 0.5 to 90 mole percent of the olefin reactant. Preferably the amount of metal iodide to be employed is between 15 to 50 mole percent of the olefin employed.

In order for the cyclic carbonate esters to be produced at a high rate, a catalytic iron compound or a catalytic copper compound or a combination of such iron and copper compounds supported on a high surface area inert support must be employed as part of the catalyst system of this process. As shown by the examples, the use of both an iron compound and a copper compound together in the catalyst system results in an increased rate of carbonate ester formation compared to the use of either the iron compound or the copper compound alone. The iron and copper compounds may be deposited independently on separate high surface area supports or they may be deposited together on the same support.

The iron compound deposited on the inert support material is preferably present in an amount corresponding to 0.01 to 20 weight percent as iron ion with respect to the support material, and is more preferably present in an amount corresponding to about 0.1 to 10 weight percent as iron ion with respect to the support material. Iron compounds suitable for deposition on the support include, for example, ferrous iodide, ferrous and ferric bromides, ferrous and ferric chlorides, ferrous and ferric nitrates, ferrous and ferric sulfates, ferrous and ferric hydroxides and oxides, and the like.

The copper compound which is deposited on the support material is preferably present in an amount corresponding to from about 0.01 to 20 weight percent as copper ion with respect to the support material, and is more preferably present in an amount corresponding to from about 0.1 to 10 weight percent as copper ion with respect to the support material. Copper compounds suitable for deposition on the support material include, for example, cupric sulfate, cuprous or cupric bromides, cuprous or cupric chlorides, cuprous iodide, cupric perchlorate, cupric nitrate, cupric acetate, cuprous and cupric carbonates, cuprous and cupric oxides, and the like.

The support material employed may be any suitable inert material. Materials suitable to be used as the catalyst support include, for example, silica, alumina, silica-alumina, titanium dioxide, zirconium dioxide, magnesium oxide, and carbon. The surface area of the support material is preferably about 10 to about 1500 $m^2/gm$ and is more preferably at least 100 $m^2/gm$.

The amount of supported iron and/or copper catalyst which is employed may be from about 0.1 to 95 weight percent with respect to the amount of olefin employed and is preferably from about 5 to 50 weight percent with respect to the amount of olefin employed.

Solvents suitable for use in the process of this invention to form the reaction medium are, for example, water or mixtures of water and a water-miscible organic solvent. Organic solvents which are suitable for use in this process include, for example, acetonitrile, N,N-dimethylformamide, dioxane, propylene-1,2-diol, sulfolane, tertiary butyl alcohol, tetrahydrofuran, and the like. The ratio of the volume of water to the volume of organic solvent which may be employed is not critical but preferably is from about 10:1 to about 1:10. More preferably it ranges between about 5:1 to about 1:5.

The reaction temperature at which the process may be operated may vary between about 50° C. and 160° C. The preferred temperature is between about 80° C. and 130° C.

The partial pressure of carbon dioxide to be employed in the process of this invention will generally vary between about 15 and 1000 psia. The preferred carbon dioxide partial pressure is between about 100 to about 700 psia.

The amount of oxygen to be employed in the process of this invention must, of course, be at least the stoichiometric amount required with respect to the starting olefin, but a stoichiometric excess of oxygen may be employed. A slight stoichiometric excess of oxygen is preferably employed in the process of this invention. The oxygen may be employed as pure oxygen, may be in the form of an oxygen-containing gas such as air, or may be diluted with an inert gas such as nitrogen, argon, etc. The partial pressure of oxygen which may be employed in the process of this invention preferably varies between about 10 and about 400 psia and is more preferably between about 50 and 200 psia. The partial pressure of oxygen should be regulated so as to avoid the formation of explosive mixtures during the course of the carboxylation reaction.

The total pressure to be used in the process of this invention may vary between about 200 to about 2000 psig. The preferred total pressure to be used in the process of this invention is between about 800 and 1600 psig.

In order to obtain a high yield of desired product the pH of the reaction should be maintained at about 4 to 8, preferably 5 to 7.

The experiments in Examples 1-3 hereinafter were carried out to illustrate the prior art processes for the direct oxidative carboxylation of olefins to produce cyclic alkylene carbonate esters. Examples 4-27 hereinafter illustrate the present invention without limiting the scope thereof which is set forth in the claims.

EXAMPLE 1

Into a 500 cc Hastelloy C stirred autoclave was introduced 14.0 g of activated manganese dioxide, 17.0 g of iodine, 60 ml of water, 80 ml of acetonitrile, 16.0 g of propylene, and 350 psia of carbon dioxide. The reaction mixture was heated at 70° C. with stirring for eight hours. After cooling the reaction mixture to 25° C., the autoclave was slowly vented. The liquid product was analyzed by gas-liquid chromatography to reveal the presence of 8 mmoles of propylene oxide, 71 mmoles of propylene carbonate, and 66 mmoles of propylene iodohydrins. The productivity rate was 0.1 mole/gm.-ion metal/hr.

EXAMPLE 2

Into the reactor described in Example 1 was introduced 10.6 g of cuprous iodide, 2.8 g of sodium nitrite, 120 ml of water, 30 ml of acetonitrile, 16.0 g of propylene, 190 psia of carbon dioxide, and 90 psia of oxygen. The reaction mixture was heated at 70° C. with stirring for three hours. After cooling to 25° C. the autoclave was vented. Gas-liquid chromatographic analysis of the liquid product revealed the presence of 2 mmoles of propylene oxide, 19 mmoles of propylene carbonate, and 10 mmoles of propylene iodohydrins. The productivity rate was 0.2 mole/gm.-ion metal/hr.

EXAMPLE 3

Into the reactor described in Example 1 was introduced 8.6 g of ferrous iodide, 3.3 g of cupric sulfate, 9.2 g of potassium iodide, 11.1 g of calcium carbonate, 120 ml of water, 30 ml of sulfolane, 16.0 g of propylene, 600 psia of carbon dioxide, and 65 psia of oxygen. The reaction mixture was heated at 120° C. with stirring for five hours. Oxygen (10 psia) was added after each hour of the reaction. After cooling the reaction mixture to 25° C., the autoclave was vented. The solid catalyst was recovered by filtration, and the liquid product was analyzed by gas-liquid chromatography to reveal the presence of 73 mmoles of propylene carbonate, 59 mmoles of propylene glycol, 13 mmoles of propylene iodohydrins, 12 mmoles of acetone, and 3 mmoles of propionaldehyde. The productivity rate was 0.8 mole/gm-ion metal/hr.

EXAMPLE 4

A 500 cc Hastelloy C autoclave was equipped with a stainless steel wire mesh cross-shaped basket attached to the shaft of the mechanical stirrer in which the catalyst was contained. To this reactor was introduced 21.0 g of catalyst consisting of 2.2 g of ferrous iodide and 0.8 g of cupric sulfate deposited on carbon which had a surface area of about 1200 $m^2/g$, 23.0 g of propylene, 37.1 g of potassium iodide, 240 ml of water, 60 ml of sulfolane, 600 psia of carbon dioxide, and 60 psia of oxygen. The reaction mixture was stirred at 120° C. for three hours. The total pressure was maintained by adding 10 psia aliquots of oxygen as required. The reaction mixture was cooled to about 25° C., and the pressure was carefully vented. Analysis of the liquid product by gas-liquid chromatography indicated the presence of 3 mmoles of propylene oxide, 3 mmoles of propionaldehyde, 17 mmoles of acetone, 13 mmoles of propylene iodohydrins, 134 mmoles of propylene glycol, and 164 mmoles of propylene carbonate. The productivity rate was 3.04 moles/gm-ion metal/hr.

EXAMPLE 5

An experiment was carried out under the same conditions as in Example 4 except that 20.3 g of a catalyst consisting of 2.1 g of ferrous iodide and 0.3 g of cupric sulfate deposited on 700 m²/g silica and 16.6 g of propylene were charged to the reactor. After three hours gas-liquid chromatography indicated the presence of 2 mmoles of propylene oxide, 0.5 mmole propionaldehyde, 1 mmole of acetone, 6 mmoles of propylene iodohydrins, 117 mmoles of propylene glycol, and 82 mmoles of propylene carbonate. The productivity rate was 8.0 mmoles/gm-ion metal/hr.

EXAMPLE 6

The procedure used in Example 4 was repeated employing 10.0 g of a catalyst consisting of 1.2 g of ferrous iodide and 0.4 g of cupric sulfate deposited on about 400 m²/g silica and 20.0 g of propylene. After three hours analysis by gas-liquid chromatography indicated the presence of 4 mmoles of propionaldehyde, 8 mmoles of acetone, 2 mmoles of propylene iodohydrins, 26 mmoles of propylene glycol, and 105 mmoles of propylene carbonate. The productivity rate was 7.6 moles/gm-ion metal/hr.

EXAMPLES 7–9

Three experiments were carried out using the same catalyst as in Example 6 following the procedure used in Example 4 except that the partial pressure of oxygen which was employed was varied, and no further oxygen was added during the course of the experiments. The experimental results are shown in Table I.

TABLE I

| Run # | 7 | 8 | 9 |
|---|---|---|---|
| Charge (grams) | | | |
| Propylene | 19.1 | 19.6 | 14.2 |
| FeI$_2$ | 1.2 | 1.2 | 1.2 |
| CuSO$_4$ | 0.4 | 0.4 | 0.4 |
| KI | 37.1 | 37.0 | 38.0 |
| O$_2$ (psia) | 39 | 108 | 136 |
| Products (mmoles) | | | |
| Propylene oxide | None | 1 | 1 |
| Propionaldehyde | 2 | 2 | 2 |
| Acetone | 5 | 4 | 8 |
| Propylene Iodohydrins | 3 | 1 | 1 |
| Propylene glycol | 5 | 17 | 22 |
| Propylene carbonate | 35 | 57 | 66 |
| Productivity Rate (moles/gm-ion metal/hr) | 2.6 | 4.3 | 5.2 |

EXAMPLES 10–13

A series of experiments were conducted using the same procedures used in Example 4 except that the catalyst used consisted of about 0.2 g of ferrous iodide and about 0.1 g of cupric sulfate per g of catalyst deposited on about 1100 m²/g carbon, the partial pressure of oxygen employed was 100 psia and no additional oxygen was added during the experiment. The partial pressure of carbon dioxide was varied. The experimental results are shown in Table II.

TABLE II

| Run # | 10 | 11 | 12 | 13 |
|---|---|---|---|---|
| Charge (grams) | | | | |
| Propylene | 27.0 | 24.6 | 21.2 | 10.1 |
| Catalyst | 15.3 | 15.5 | 14.5 | 15.0 |
| FeI$_2$ | 2.5 | 2.6 | 2.4 | 2.5 |
| CuSO$_4$ | 1.3 | 1.3 | 1.2 | 1.3 |
| KI | 38.0 | 38.1 | 37.5 | 38.2 |
| CO$_2$ (psia) | 100 | 300 | 400 | 550 |
| Reaction Time (hours) | 5 | 3 | 5 | 5 |
| Products (mmoles) | | | | |
| Propionaldehyde | 4 | 3 | 3 | 2 |
| Acetone | 20 | 11 | 12 | 10 |
| Propylene iodohydrins | 4 | 2 | 2 | 2 |
| Propylene glycol | 50 | 26 | 47 | 55 |
| Propylene carbonate | 73 | 60 | 92 | 99 |
| Productivity Rate (moles/gm-ion metal/hr) | 1.9 | 2.1 | 2.0 | 2.1 |

EXAMPLES 14–16

A series of experiments was conducted using 6.6 g of the same catalyst employed in Examples 10–13. The experimental conditions were essentially the same as described in Example 4 except that the partial pressure of oxygen employed was 100 psia, and the amount of potassium iodide included in the charge was varied. The experimental results are shown in Table III.

TABLE III

| Run # | 14 | 15 | 16 |
|---|---|---|---|
| Charge (grams) | | | |
| Propylene | 22.1 | 16.0 | 23.4 |
| FeI$_2$ | 1.1 | 1.1 | 1.1 |
| CuSO$_4$ | 0.6 | 0.6 | 0.6 |
| KI | 5.2 | 24.7 | 124.6 |
| Reaction Time (hours) | 5 | 4 | 5 |
| Products (mmoles) | | | |
| Propylene oxide | Trace | None | 2 |
| Propionaldehyde | 1 | 1 | Trace |
| Acetone | 4 | 2 | 2 |
| Propylene iodohydrins | 1 | 1 | 2 |
| Propylene glycol | 7 | 21 | 124 |
| Propylene carbonate | 24 | 27 | 34 |
| Productivity Rate (moles/gm-ion metal/hr) | 1.0 | 1.9 | 4.9 |

EXAMPLES 17–20

A series of experiments was carried out in which the reaction temperature was varied. The catalyst which was employed consisted of 0.006 g of ferrous iodide and 0.015 g of cupric sulfate per gram of catalyst deposited on about 1200 m²/g surface area carbon. The experimental conditions employed were essentially the same as described in Example 4 except that the oxygen partial pressure employed was 200 psia and the reaction time was four hours. The experimental results are shown in Table IV.

TABLE IV

| Run # | 17 | 18 | 19 | 20 |
|---|---|---|---|---|
| Charge (grams) | | | | |
| Propylene | 24.0 | 15.7 | 17.8 | 18.7 |
| Catalyst | 13.2 | 13.7 | 16.2 | 12.7 |
| KI | 38.1 | 37.5 | 37.7 | 38.6 |
| Reaction Temperature (°C.) | 80 | 100 | 120 | 140 |
| Products (mmoles) | | | | |
| Propionaldehyde | 1 | 1 | 1 | 1 |
| Acetone | 2 | 3 | 2 | 4 |
| Propylene iodohydrins | 1 | 1 | 1 | 1 |
| Propylene glycol | 2 | 9 | 49 | 89 |
| Propylene carbonate | 8 | 28 | 50 | 49 |
| Productivity Rate (moles/gm-ion metal/hr) | 2.3 | 6.8 | 14.0 | 25.2 |

EXAMPLES 21-26

A series of experiments was carried out to illustrate the variety of supported iron and copper compounds which can be employed as catalysts for use in this process. The catalysts were employed as suspended slurries in the liquid reaction mixture. The reactor was a 300 cc Hastelloy C autoclave equipped with an impeller-type stirrer. The reaction conditions and experimental results are shown in Table V.

TABLE V

| Run # | 21 | 22 | 23 | 24 | 25 | 26 |
|---|---|---|---|---|---|---|
| Charge (grams) | | | | | | |
| Propylene | 20.4 | 18.0 | 18.8 | 16.6 | 9.8 | 9.3 |
| Catalyst | 5.0 | 5.0 | 2.5 + 2.5 | 5.0 | 3.3 | 3.0 |
| Fe compound | 0.4 | None | 0.2 | None | None | 0.5 |
| Cu compound | None | 0.4 | 0.2 | 0.4 | 0.4 | 0.2 |
| KI | 18.5 | 18.5 | 18.5 | 18.5 | 12.3 | 12.3 |
| $H_2O$ (mls) | 150 | 150 | 140 | 150 | 100 | 95 |
| $CO_2$ (psia) | 600 | 600 | 600 | 600 | 600 | 600 |
| $O_2$ (psia) | 60 | 60 | 60 | 60 | 60 | 60 |
| Reaction Temperature (°C.) | 120 | 120 | 120 | 120 | 120 | 120 |
| Reaction Time (hours) | 5 | 5 | 5 | 5 | 5 | 5 |
| Products (mmoles) | | | | | | |
| Propylene oxide | 2 | Trace | Trace | Trace | Trace | Trace |
| Propionaldehyde | 3 | 2 | 2 | Trace | 1 | 1 |
| Acetone | 27 | 8 | 19 | 1 | 4 | 7 |
| Propylene iodohydrins | 3 | 2 | 5 | 5 | Trace | 1 |
| Propylene glycol | 7 | 15 | 11 | 7 | 10 | 16 |
| Propylene carbonate | 20 | 51 | 46 | 21 | 18 | 41 |
| Productivity Rate (moles/gm-ion metal/hr) | 5.4 | 5.2 | 6.2 | 4.1 | 3.2 | 4.3 |

| Run # | Catalyst Description |
|---|---|
| 21 | $FeCl_3/SiO_2$ |
| 22 | $CuCl_2/SiO_2$ |
| 23 | $FeCl_3 + CuCl_2/SiO_2$ |
| 24 | $CuCO_3 \cdot Cu(OH)_2/SiO_2$ |
| 25 | $CuI/SiO_2$ |
| 26 | $Fe(NO_3)_3 + Cu(NO_3)_2/SiO_2$ |

EXAMPLE 27

An experiment was carried out using 10.0 g of a catalyst comprised of 1.4 g of ferrous iodide and 1.0 g of cupric sulfate deposited on about 400 m²g silica following the same procedure as in Example 4 except that 41.7 g of 1-butene was the olefin employed and the oxygen partial pressure was 150 psia. After stirring for three hours gas-liquid chromatography of the liquid product indicated the presence of 2 mmoles of butene-1,2-epoxide, 1 mmole of n-butyraldehyde, 5 mmoles of 2-butanone, 1 mmole of 1-butene iodohydrins, 29 mmoles of butane-1,2-diol, and 93 mmoles of the cyclic carbonate ester of butane-1,2-diol. The productivity rate was 4.1 moles/gm-ion metal/hr.

What is claimed is:

1. A process for the preparation of a cyclic alkylene carbonate ester which comprises reacting in a liquid phase a cyclic or linear olefin having from 2 to 15 carbon atoms with carbon dioxide at a temperature of from 50° to 160° C., at a total pressure of from 200 to about 2,000 psig and a pH value of between about 4 and 8, in the presence of oxygen or an oxygen-containing gas and a catalytic amount of a mixture of
   (a) iodine or an iodide of a metal selected from Groups IA, IB, IIA, IIB, VB, VIIB, and VIII of the Periodic Table of Elements and
   (b) A catalytic iron compound, copper compound or mixture thereof deposited on an inert supporting material, and recovering the desired cyclic alkylene carbonate ester.

2. The process of claim 1 wherein said olefin is propylene.

3. The process of claim 1 wherein (a) is selected from the group consisting of iodine, lithium iodide, potassium iodide, cuprous iodide, calcium iodide, magnesium iodide, zinc iodide, cadmium iodide, vanadium iodide, manganese iodide, iron iodide and cobalt iodide.

4. The process of claim 1 wherein (a) is present in an amount of from 0.5 to 90 mole percent of said olefin reactant.

5. The process of claim 1 wherein (b) is a mixture of said catalytic iron compound and said catalytic copper compound deposited on an inert supporting material.

6. The process of claim 1 wherein (b) is present in an amount of from about 0.1 to 95 mole percent of said olefin reactant.

7. The process of claim 1 wherein said total pressure is from about 800 to 1,600 psig.

* * * * *